United States Patent
Dudding et al.

(10) Patent No.: US 7,660,630 B2
(45) Date of Patent: Feb. 9, 2010

(54) VARIABLE IMPLANTABLE MEDICAL DEVICE POWER CHARACTERISTICS BASED UPON IMPLANT DEPTH

(75) Inventors: Charles H. Dudding, Lino Lakes, MN (US); Gregory J. Haubrich, Champlin, MN (US); Javaid Masoud, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 473 days.

(21) Appl. No.: 11/380,445

(22) Filed: Apr. 27, 2006

(65) Prior Publication Data

US 2007/0255318 A1   Nov. 1, 2007

(51) Int. Cl.
*A61N 1/00* (2006.01)
(52) U.S. Cl. .......................................... 607/27; 607/32
(58) Field of Classification Search ............. 607/27–32, 607/59–62
See application file for complete search history.

(56) References Cited

U.S. PATENT DOCUMENTS

| | | | |
|---|---|---|---|
| 4,401,119 A | 8/1983 | Herpers | |
| 5,331,966 A | 7/1994 | Bennett et al. | |
| 5,345,362 A | 9/1994 | Winkler | |
| 5,476,488 A * | 12/1995 | Morgan et al. | 607/30 |
| 5,562,713 A | 10/1996 | Silvian | |
| 5,564,434 A | 10/1996 | Halperin et al. | |
| 5,683,432 A | 11/1997 | Goedeke et al. | |
| 5,807,336 A | 9/1998 | Russo et al. | |
| 5,843,139 A | 12/1998 | Goedeke et al. | |
| 5,944,745 A | 8/1999 | Rueter | |
| 6,073,050 A | 6/2000 | Griffith | |
| 6,201,993 B1 * | 3/2001 | Kruse et al. | 607/30 |
| 6,766,198 B1 | 7/2004 | Snell | |
| 2005/0197680 A1 | 9/2005 | DelMain et al. | |
| 2005/0251579 A1 | 11/2005 | Ngo et al. | |

* cited by examiner

*Primary Examiner*—Scott M Getzow
(74) *Attorney, Agent, or Firm*—Michael J. Ostrom; Stephen W. Bower

(57) ABSTRACT

An implantable medical device ("IMD") as described herein includes adjustable power characteristics such as variable transmitter output power and variable receiver front end gain. These power characteristics are adjusted based upon the intended or actual implant depth of the IMD. The IMD may process an IMD implant depth value (provided by an external IMD programming device) to generate power scaling instructions or control signals that are interpreted by the IMD transmitter and/or the IMD receiver. Such adjustability enables the IMD to satisfy minimum telemetry requirements in a manner that does not waste power, thus extending the IMD battery life.

20 Claims, 6 Drawing Sheets

VARIABLE IMPLANTABLE MEDICAL DEVICE POWER CHARACTERISTICS BASED UPON IMPLANT DEPTH

TECHNICAL FIELD

The present invention relates generally to implantable medical devices ("IMDs"). More particularly, the present invention relates to power management techniques for use with IMDs.

BACKGROUND

IMDs are used to treat patients suffering from a variety of conditions. Examples of IMDs involving cardiac devices are implantable pacemakers and implantable cardioverter-defibrillators ("ICDs"). Such electronic medical devices generally monitor the electrical activity of the heart and provide electrical stimulation to one or more of the heart chambers when necessary. For example, pacemakers provide appropriate electrical stimulation pulses at a controlled rate to selected chambers of the heart in order to control rate and/or correct the arrhythmias.

ICDs also detect arrhythmias and provide appropriate electrical stimulation pulses to selected chambers of the heart to correct an abnormal heart rate. In contrast to pacemakers, however, an ICD can also provide pulses that are much stronger and less frequent, where such pulses are generally designed to correct fibrillation, which is a rapid, unsynchronized quivering of one or more heart chambers, and severe tachycardias, during which the heartbeats are very fast but coordinated. To correct such arrhythmias, ICDs deliver low, moderate, or high-energy therapy pulses to the heart.

Generally, IMDs include on-board memory in which telemetered signals can be stored for later retrieval and analysis. Typically, the telemetered signals provide patient physiologic and cardiac information. This information is generally recorded on a per heartbeat, binned average basis, or derived basis, and involve, for example, atrial electrical activity, ventricular electrical activity, minute ventilation, patient activity score, cardiac output score, mixed venous oxygen score, cardiovascular pressure measures, time of day, and any interventions and the relative success of such interventions. Telemetered signals can also be stored in a broader class of monitors and therapeutic devices for other areas of medicine, including metabolism, endocrinology, hematology, neurology, muscular disorders, gastroenterology, urology, ophthalmology, otolaryngology, orthopedics, and similar medical subspecialties.

Generally, upon detecting arrhythmias and, when necessary, providing corresponding therapies to correct such arrhythmias, IMDs store the telemetered signals over a set period of time (usually before, during, and after the occurrence of such arrhythmic event). Current practice in the art involves the use of an external communication unit, e.g., an external programmer, for non-invasive communication with IMDs via uplink and downlink communication channels associated with the communication device. In accordance with conventional medical device programming systems, a programming head can be used for facilitating two-way communication between IMDs and the external communication device. In many known IMD systems, the programming head can be positioned on the patient's body over the IMD side such that the programming head can send wireless signals to, and receive wireless signals from, the IMD in accordance with common practice in the art.

Implementation and operation of most, if not all, RF communication systems for IMDs and external communication devices involves a balancing or compromising of certain countervailing considerations, relating to such interrelated operational parameters as data transmission rate, transmission range, IMD power consumption and battery life, among numerous others. Such operational parameters are often interrelated in the sense that the adjustment of one operating parameter may permit or require the adjustment of one or more other operating parameters even while predetermined system performance goals and/or requirements continue to be met and predetermined limitations imposed upon operational parameter adjustment are adhered to. For example, to meet a minimum transmission range, the transmitter output power of an IMD must provide telemetry signals having sufficient energy.

Conventional IMDs are limited in that they typically operate with fixed power characteristics. Moreover, power characteristics of IMDs are usually set with the assumption that the IMD will be implanted at a relatively deep implant depth beneath the patient's skin, such as six or more centimeters. Consequently, when implanted at relatively shallow depths, such IMDs will transmit telemetry signals using more power than is necessary, resulting in wasted transmitter output power and decreased battery life.

Accordingly, it is desirable to have an IMD equipped with variable power characteristics that can be adjusted in response to an intended, desired, or actual IMD implant depth. Furthermore, other desirable features and characteristics of the present invention will become apparent from the subsequent detailed description and the appended claims, taken in conjunction with the accompanying drawings and the foregoing technical field and background.

BRIEF SUMMARY

An IMD as described herein can optimize its battery life according to its implant depth—relatively shallow IMDs need not transmit telemetry signals using high power that might otherwise be necessary for relatively deep IMDs. An IMD as described herein may also utilize a quality of service monitor to ensure that its implant-depth-dependent power characteristics result in telemetry communications that satisfy minimum quality of service parameters.

The above and other aspects of the invention may be carried out in one form by a method for operating an IMD. The method involves: receiving an IMD implant depth value that is indicative of an implant depth measurement for the IMD; performing a power scaling routine for the IMD based upon the IMD implant depth value; and adjusting power characteristics of the IMD in response to the power scaling routine.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

Figure 1:
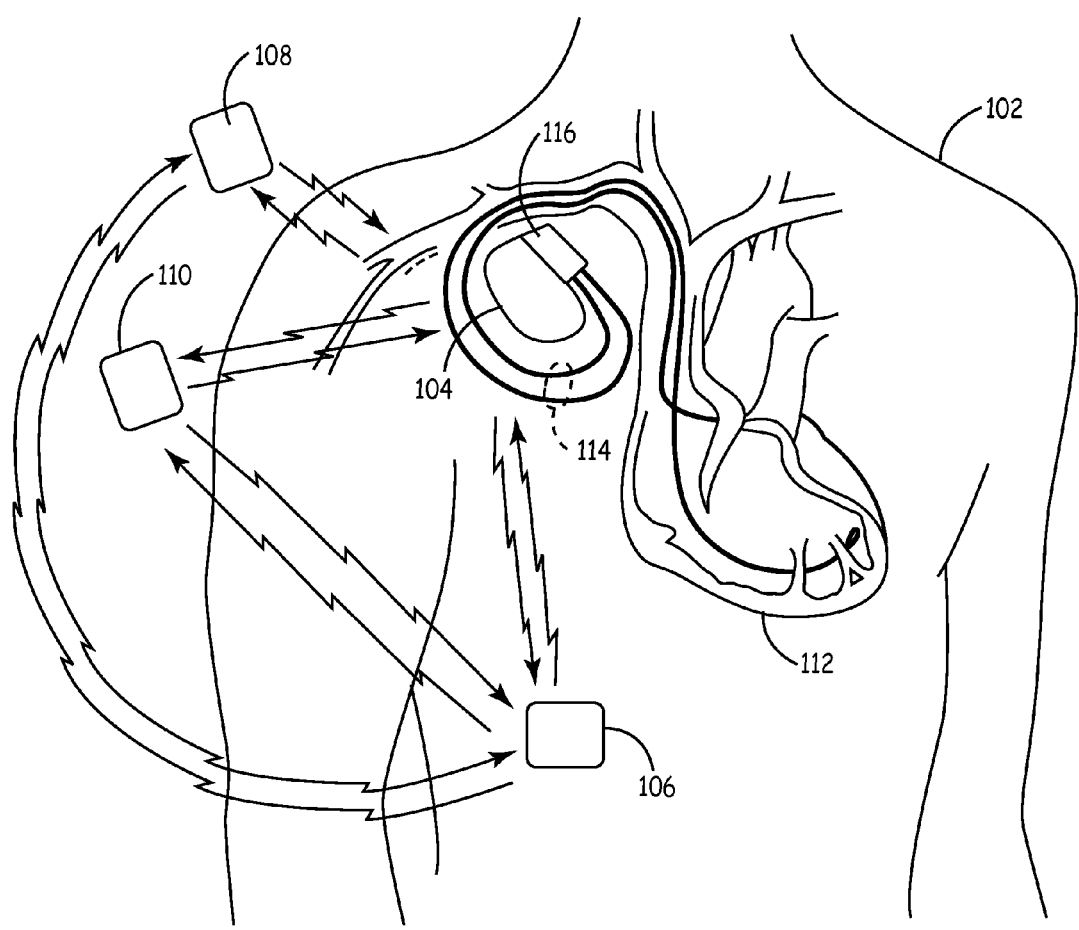
FIG. 1 is an illustration of a system including an IMD in accordance with certain embodiments of the invention.

The following detailed description is merely illustrative in nature and is not intended to limit the invention or the application and uses of the invention. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present invention may be practiced in conjunction with any number of data transmission protocols and that the system described herein is merely one exemplary application for the invention.

For the sake of brevity, conventional techniques and features related to IMDs, IMD telemetry, signal processing, data transmission, signaling, IMD transceivers, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

The following description refers to elements or features being "connected" or "coupled" together. As used herein, unless expressly stated otherwise, "connected" means that one element/feature is directly joined to (or directly communicates with) another element/feature, and not necessarily mechanically. Likewise, unless expressly stated otherwise, "coupled" means that one element/feature is directly or indirectly joined to (or directly or indirectly communicates with) another element/feature, and not necessarily mechanically. Thus, although the figures may depict example arrangements of elements, additional intervening elements, devices, features, or components may be present in an actual embodiment (assuming that the functionality of the device/system is not adversely affected).

The embodiments of the present invention can be implemented with any IMD having wireless telemetry capabilities. At present, a wide variety of IMDs are commercially available or proposed for clinical implantation. Such IMDs include pacemakers as well as ICDs, drug delivery pumps, cardiomyostimulators, cardiac and other physiologic monitors, nerve and muscle stimulators, deep brain stimulators, cochlear implants, and artificial organs (e.g., artificial hearts). In addition, as the technology advances, it is contemplated that IMDs shall become even more complex with respect to programmable operating modes, menus of operating parameters, and monitoring capabilities of increasing varieties of physiologic conditions and electrical signals. It is to be appreciated that embodiments of the present invention will be applicable in such emerging IMD technology as well. Further, the embodiments of the invention can be implemented in more than one IMD implanted within the same patient to enable telemetry communication between the IMDs.

FIG. 1 illustrates bi-directional telemetry communication involving one or more IMDs in accordance with certain embodiments of the invention. FIG. 1 generally represents a body area network system 100 having multiple devices configured to communicate with one another. As used herein, a "body area network" is a localized network of communicating devices associated with a single patient 102, where devices within the body area network are suitably configured to communicate with each other using one or more data communication protocols. A body area network device may be an IMD, a device affixed to the patient (such as a physiologic characteristic sensor or monitor), a device worn or held by the patient (such as a remote control device for an IMD, a wireless monitor device for an IMD, or a handheld programmer for an IMD), or a device in close proximity to the patient (such as an external programmer that communicates with an IMD). In this example, system 100 generally includes an IMD 104 implanted within patient 102, another IMD 106 implanted within patient 102, and two external communication devices 108/110 that are not implanted within patient 102.

In certain embodiments communications can take place between IMD 104 and any number of the devices within system 100. Moreover, telemetry communications may take place between devices (other than IMD 104) within system 100. The arrows in FIG. 1 represent such telemetry communications. In practice, a given communication session between two devices in system 100 may be unidirectional or bidirectional (in this example, FIG. 1 depicts bidirectional communications). In certain embodiments, the electrical devices can include one or more of at least one implantable medical instrumentation and of at least one external communication device. As shown in FIG. 1, in certain embodiments, the at least one implantable medical instrumentation can include IMD 104 and IMD 106, and the at least one external communication device can include external communication devices 108 and 110; however, it is to be appreciated that such quantities are not provided to limit the scope of application of embodiments of the invention.

In certain embodiments, when IMD 104 is used for cardiac applications (e.g., to provide cardiac sensing and pacing functions for patient 102), IMD 104 can be a cardiac device; for example, a pacemaker, an ICD, a hemodynamic monitor, or the like. As described above, however, neither IMD 104 nor any of the devices within system 100 should be limited to such applications or such devices. In this example, IMDs 104/106 are implanted in the same patient 102 beneath the patient's skin or muscle and, in certain embodiments, IMDs 104/106 can be typically oriented to the skin surface. In certain embodiments, when IMD 104 is used for cardiac applications, as shown, IMD 104 is electrically coupled to the heart 112 of the patient 102 through pace/sense or cardioversion/defibrillation electrodes operatively coupled to lead conductor(s) of one or more endocardial leads 114, which in turn, are coupled to a connector block 116 of IMD 104 in a manner well known in the art.

As generally mentioned above, among other design functions, each of the external communication devices 108/110 is designed for non-invasive communication with one or more of the IMDs 104/106, where such communication is enabled via downlink and uplink communication channels, which will be further described below. In certain embodiments, one or more of the external communication devices 108/110 can be an external pressure reference monitor ("EPR"). An EPR is typically used to derive reference pressure data for use in combination with absolute pressure derived from an IMD. In addition, an EPR measures and records barometric pressure which is necessary for correlation to atmospheric pressure. However, it is to be appreciated that embodiments of the invention are not limited to such EPR applications. Generally, any form of portable programmer, interrogator, recorder, monitor, or telemetered signals transmitter and/or receiver found suitable for communicating with IMD 104 and/or IMD 106, in turn, could be used for external communication devices 108/110.

Figure 2:
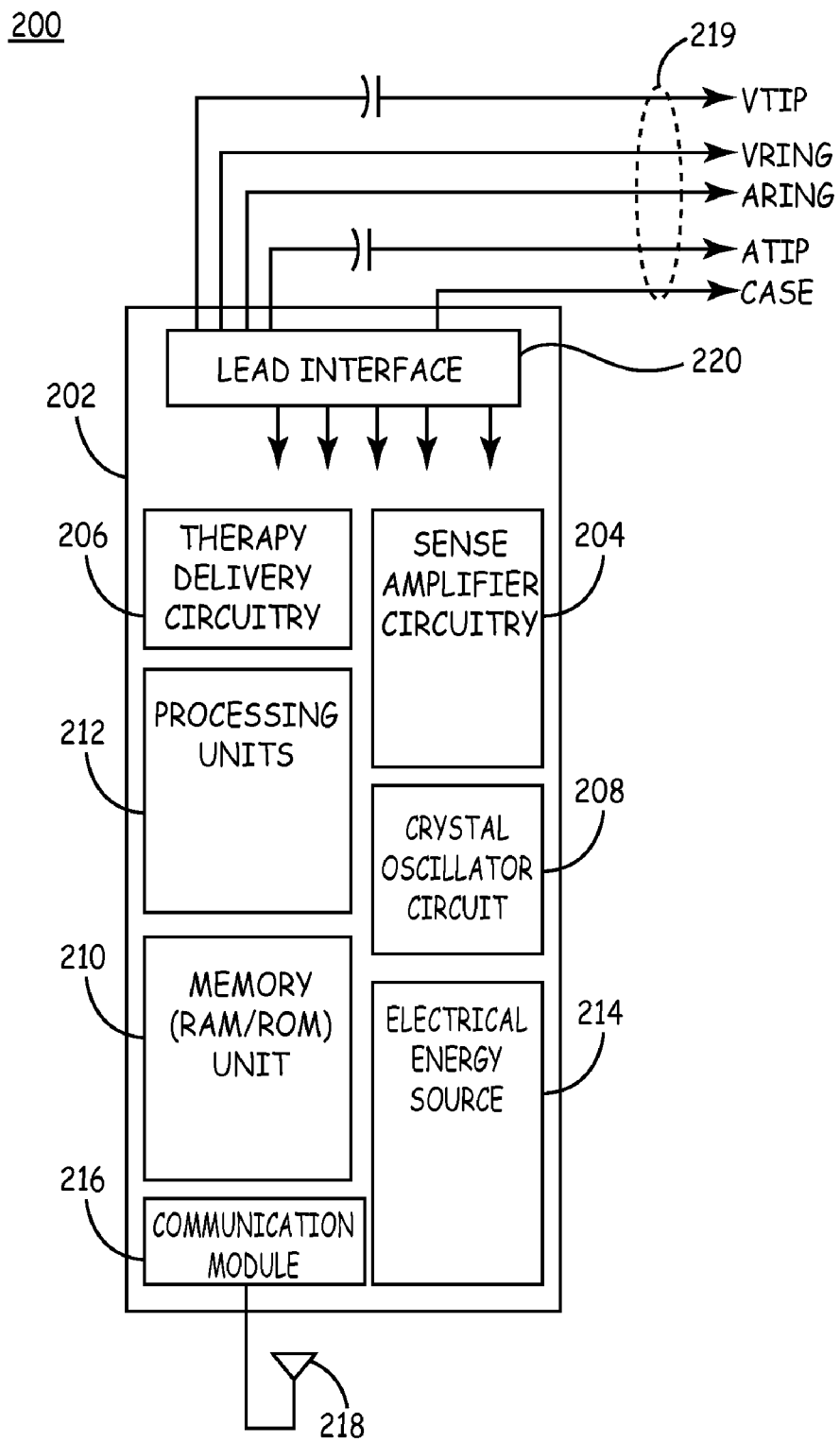
FIG. 2 is a block diagram of example circuitry of an IMD suitable for use in the system depicted in FIG. 1.

FIG. 2 shows an exemplary block diagram of the electronic circuitry of an IMD 200 configured in accordance with certain embodiments of the invention. IMD 104, IMD 106, and/or any other IMD implanted in patient 102 may be configured as shown in FIG. 2. As can be seen from FIG. 2, IMD 200 includes primary circuitry 202 for managing the operation and function of IMD 200, with such primary circuitry 202 being contained within a hermetic enclosure of IMD 200. The primary circuitry 202 includes a number of electrical components, most of which are exemplified in U.S. Pat. No. 6,539,253, entitled "Implantable Medical Device Incorporating Integrated Circuit Notch Filters" (incorporated herein by reference in relevant part). In certain embodiments, the primary circuitry 202 in FIG. 2 includes, without limitation: sense amplifier circuitry 204; therapy delivery circuitry 206; a crystal oscillator circuit 208; a suitable amount of memory 210, which may include random-access memory (RAM) and/or read-only memory (ROM); a processing unit 212; and an electrical energy source 214. In certain embodiments, the primary circuitry 202 also includes a communication module 216 and one or more antennas 219 configured to enable IMD 200 to communicate with other devices within and/or outside the body area network. It should be appreciated that the below descriptions of the primary circuitry 202 within the IMD 200 are merely example configurations.

In certain embodiments, when IMD 200 is used for cardiac applications (e.g., to provide cardiac sensing and pacing functions for the patient), the IMD 200 is coupled to the one or more endocardial leads 219 which, when implanted, extend transvenously between the implant site of the IMD 200 and the patient's heart, as previously noted with reference to FIG. 1. As mentioned above, the physical connections between the leads 219 and the various internal components of IMD 200 are facilitated by means of a conventional connector block assembly. Electrically, the coupling of the conductors of the leads 219 and internal electrical components of IMD 200 may be facilitated by means of a lead interface circuit 220 which functions, in a multiplexer-like manner, to selectively and dynamically establish necessary connections between various conductors in the leads 219 and individual electrical components of the IMD 200, as would be familiar to those of ordinary skill in the art. In certain embodiments, with respect to such cardiac applications, the various conductors in the leads 219 can include atrial tip and ring electrode conductors, $A_{TIP}$ and $A_{RING}$, and ventricular tip and ring electrode conductors, $V_{TIP}$ and $V_{RING}$. For the sake of clarity, the specific connections between the leads 219 and the various components of the IMD 200 are not shown in FIG. 2, although such connections will be familiar to those of ordinary skill in the art. For example, in cardiac applications, the leads 219 will necessarily be coupled, either directly or indirectly, to the sense amplifier circuitry 204 and the therapy delivery circuitry 206, in accordance with common practice, such that cardiac electrical signals may be conveyed to the sense amplifier circuitry 204 and such that stimulating pulses may be delivered by the therapy delivery circuitry 206 to cardiac tissue, via the leads 219. Also not shown in FIG. 2 is the protection circuitry commonly included in implanted devices to protect, for example, the sensing circuitry of the device from high voltage stimulating pulses.

As previously noted, the primary circuitry 202 includes the processing unit 212 which generally varies in sophistication and complexity depending upon the type and functional features of the IMD 200. In certain embodiments, the processing unit 212 can be an off-the-shelf programmable microprocessor, a microcontroller, a custom integrated circuit, or any of a wide variety of other implementations generally known. Although specific connections between the processing unit 212 and other components of the IMD 200 are not shown in FIG. 2, it will be apparent to those of ordinary skill in the art that the processing unit 212 functions to control the timed operation of the sense amplifier circuitry 204 and the therapy delivery circuitry 206. In certain embodiments, the functioning of the processing unit 212 would be under control of firmware and programmed software algorithms stored in memory 210 (e.g., RAM, ROM, PROM and/or reprogrammable ROM) and are carried out using a processing unit of a typical microprocessor core architecture. In certain embodiments, the processing unit 212 can also include a watchdog circuit, a DMA controller, a lock mover/reader, a CRC calculator, and other specific logic circuitry coupled together by on-chip bus, address bus, and power, clock, and control signal lines in paths or trees in a manner well known in the art.

In certain embodiments, as is known in the art, the electrical energy source 214 powers the primary circuitry 202 and can also be used to power electromechanical devices, such as valves or pumps, of a substance delivery IMD, or to provide electrical stimulation energy of an ICD shock generator, cardiac pacing pulse generator, or other electrical stimulation generator. In certain embodiments, the electrical energy source 214 is a high energy density, low voltage battery coupled with a power supply circuit having power-on-reset ("POR") capability. The power supply circuit provides one or more low voltage power supply signals, the POR signal, one or more voltage reference sources, current sources, an elective replacement indicator ("ERI") signal, and, in the case of an ICD, high voltage power to the therapy delivery circuitry 206. For the sake of clarity in the example block diagram provided in FIG. 2, the connections between the electrical energy source 214 and the electrical components of the IMD 200 are not shown, as one skilled in the art would be familiar with such connections.

In certain embodiments, the sense amplifier circuitry 204 can be configured to process physiologic signals that are used to trigger or modulate therapy delivery and are stored as physiologic signal data for later retrieval as described herein. Generally, the sense amplifier circuitry 204 is coupled to electrical signal sense electrodes and/or physiologic sensors on or in the housing of the IMD 200 or as mentioned above, situated at sites distanced from the IMD housing, typically in distal portions of the elongated leads 219. As is generally known, the sensors or electrodes located outside the housing are coupled by conductors to feedthrough pins of feedthroughs extending through the housing wall. Certain physiologic sensors or sense electrodes can be mounted to a connector assembly so that the conductors are quite short.

In certain embodiments, the conductors include the elongated conductors of the leads 219 extending to the remotely situated physiologic sensors and sense electrodes. As such, in some cardiac applications, the sense amplifier circuitry 204 is designed to receive electrical cardiac signals from the leads 219 and to process such signals to derive event signals reflecting the occurrence of specific cardiac electrical events, including atrial contractions (P-waves) and ventricular contractions (R-waves). These event-indicating signals are provided to the processing unit 212 for use in controlling the synchronous stimulating operations of the IMD 200 in accordance with common practice in the art. In addition, these event indicating signals may be communicated, via uplink transmission, to one or more external communication devices.

In example embodiments, the therapy delivery circuitry 206 can be configured to deliver electrical stimulation to the patient, e.g., cardioversion/defibrillation therapy pulses and/or cardiac pacing pulses delivered to the heart, or other electrical stimulation delivered to the brain, other organs, selected nerves, the spinal column, the cochlea, or muscle groups, including skeletal muscle wrapped about the heart. Alternatively, in certain embodiments, the therapy delivery circuitry 206 can be configured as a drug pump delivering drugs into organs for therapeutic treatment or into the spinal column for pain relief. Alternatively, in certain embodiments, the therapy delivery circuitry 206 can be configured to operate an implantable heart assist device or pump implanted in patients awaiting a heart transplant operation.

When the IMD 200 is used for cardiac applications, the sense amplifier circuitry 204 may also include patient activity sensors or other physiologic sensors for sensing the need for cardiac output and modulating pacing parameters accordingly through many alternative approaches set forth in the prior art. If the IMD 200 is an ICD, the therapy delivery circuitry 206 generally includes one or more high power cardioversion/defibrillation output capacitors, electronic circuitry coupled to the sense amplifiers for detecting and discriminating pathologic and/or nonpathologic arrhythmias from one another and providing other functions, high voltage electronic circuitry for charging the output capacitor(s) from a battery voltage to a higher voltage, and electronic switching circuitry for dumping the charge built up on the output capacitor(s) through the cardioversion/defibrillation electrodes operatively coupled to the one or more endocardial leads 219. Such IMDs are described in detail in U.S. Pat. Nos. 5,626,620 and 5,931,857.

Registers of the memory 210 can be used for storing data compiled from sensed cardiac activity and/or relating to device operating history or sensed physiologic parameters. Generally, the data storage can be triggered manually by the patient, on a periodic basis, or by detection logic (e.g., within the sense amplifier circuitry 204) upon satisfaction of certain programmed-in event detection criteria. If not manually triggered, in certain embodiments, the criteria for triggering data storage within the IMD 200 is programmed via telemetry transmitted instructions and parameter values. If manually triggered, in some cases, the IMD 200 includes a magnetic field sensitive switch (this may be a Hall effect sensor, or another received communications signal) that closes in response to a magnetic field, and the closure causes a magnetic switch circuit to issue a switch closed ("SC") signal to the processing unit 212 which responds in a "magnet mode." For example, the patient may be provided with a magnet (e.g., incorporated into an external communication device) that can be applied over the IMD 200 to close the switch and prompt the processing unit 212 to store physiologic episode data when the patient experiences certain symptoms and/or deliver a therapy to the patient. Following such triggering, in certain embodiments, event related data, e.g., the date and time, may be stored along with the stored periodically collected or patient initiated physiologic data. Typically, once stored, the data is ready for telemetry transmission on receipt of a retrieval or interrogation instruction.

Memory 210 may also be used to store data necessary to support the power adjustment procedures described herein. For example, memory 210 may be configured to store IMD implant depth values that are processed by IMD 200 and QoS parameters that are processed by IMD 200. Memory 210 may also be configured to store power scaling instructions, scaling control signals, or power scaling settings for the transmitter and/or receiver of IMD 200.

In certain embodiments, the crystal oscillator circuit 208 generally employs clocked CMOS digital logic ICs having a clock signal provided by a crystal (e.g., piezoelectric) and a system clock coupled thereto as well as discrete components, e.g., inductors, capacitors, transformers, high voltage protection diodes, and the like that are mounted with the ICs to one or more substrate or printed circuit board. Typically, each clock signal generated by the system clock is routed to all applicable clocked logic via a clock tree. In certain embodiments, the system clock provides one or more fixed frequency clock signals that are independent of the battery voltage over an operating battery voltage range for system timing and control functions and in formatting telemetry signal transmissions. Again, the lines over which such clocking signals are provided to the various timed components of the IMD 200 (e.g., processing unit 212) are omitted from FIG. 2 for the sake of clarity.

Those of ordinary skill in the art will appreciate that IMD 200 may include numerous other components and subsystems, for example, activity sensors and associated circuitry. The presence or absence of such additional components in IMD 200, however, is not believed to be pertinent to the present invention, which relates to the implementation and operation of a communication subsystem in the IMD 200, and associated communication subsystems in one or more of further implantable medical instrumentation and other electrical devices, such as external communication devices.

In certain embodiments, the IMD 200 can involve an implantable cardiac monitor without therapy delivery system 206, e.g., an implantable EGM monitor for recording the cardiac electrogram from electrodes remote from the heart as disclosed in U.S. Pat. No. 5,331,966. Alternatively, the IMD 200 can involve an implantable hemodynamic monitor ("IHM") for recording cardiac electrogram and other physiologic sensor derived signals, e.g., one or more of blood pressure, blood gases, temperature, electrical impedance of the heart and/or chest, and patient activity. The MEDRONIC® REVEAL® insertable loop recorder, having EGM electrodes spaced across its housing, is an example of the former, and the MEDRONIC® CHRONICLE® IHM, coupled with a capacitive pressure and temperature sensing lead and EGM sense electrodes of the type described in U.S. Pat. No. 5,564,434 is an example of the latter.

As described above, the IMD 200 includes communication module 216 and one or more antennas 218. Communication module 216 may include any number of transmitters, any number of receivers, and/or any number of transceivers, depending upon the particular implementation. As described in more detail below, IMD 200 may include power scaling logic, which may be realized in or executed by communication module 216, processing unit 212, memory unit 210, and/or elsewhere in IMD 200. In certain embodiments, each of the antennas 218 is mounted to the IMD 200 in one or more of a wide variety of configurations. For example, one or more of the antennas 218 can take the form of a surface mounted antenna (e.g., as described in U.S. Pat. No. 4,401,119, or one or more of the antennas 218 can be enclosed within or mounted to the IMD connector block assembly. However, it is to be appreciated that the invention should not be limited to such.

It is desirable to reduce the size of the IMD 200 while increasing its functional capabilities and prolonging battery life to increase longevity. In this regard, IMD 200 may be suitably configured to adjust its power characteristics as needed in response to information related to an intended, actual, or desired implant depth. For example, the gain or output power of the transmitter(s) in IMD 200 may be adjusted upwardly or downwardly according to the implant depth. In accordance with certain embodiments, the current consumption of certain transceiver circuits can also be increased or decreased to accomplish that goal.

By way of background, the IMD telemetry system and functions are described as follows. For convenience of description, the embodiments described as follows use short range RF downlink telemetry transmissions and uplink telemetry transmissions, but it should be appreciated that the embodiments of the invention should not be limited to such. Similarly, the terms "telemeter," "telemetry transmission," and the like are intended to embrace any such action and manner of communicating and conveying data and commands between the IMD 200 and other electrical devices (e.g., other IMDs implanted within the same patient, external communication devices carried or worn by the patient, and/or external monitoring devices) in the uplink transmission direction and the downlink transmission direction.

In the IMD 200, uplink and downlink telemetry capabilities are provided to enable communication with other devices. IMD 200 may be configured to communicate in a conventional manner with one or more external electrical devices, a telemetry communication device, a more proximal medical device on the patient's body, or other implantable medical instrumentation in the patient's body. Generally, the stored physiologic data as well as one or more of real-time generated physiologic data and non-physiologic data (collectively referred to herein as "patient data") can be transmitted by uplink RF telemetry from the IMD 200 to the other devices or instrumentation in response to a downlink telemetered interrogation command, events within the IMD 200 or the patient, magnet swipe across the IMD 200 by the patient, upon satisfaction of certain programmed-in event detection criteria and/or timed events. The real-time physiologic data can include real time sampled signal levels, e.g., intracardiac electrocardiogram amplitude values, and sensor output signals. The non-physiologic patient data can include currently programmed device operating modes and parameter values, battery condition, device ID, patient ID, implantation dates, device programming history, real time event markers, and the like. In the context of implantable pacemakers and ICDs, such patient data can include programmed sense amplifier sensitivity, pacing or cardioversion pulse amplitude, energy, and pulse width, pacing or cardioversion lead impedance, programmed setting, and/or accumulated statistics related to device performance, e.g., data related to detected arrhythmia episodes and applied therapies.

Figure 3:
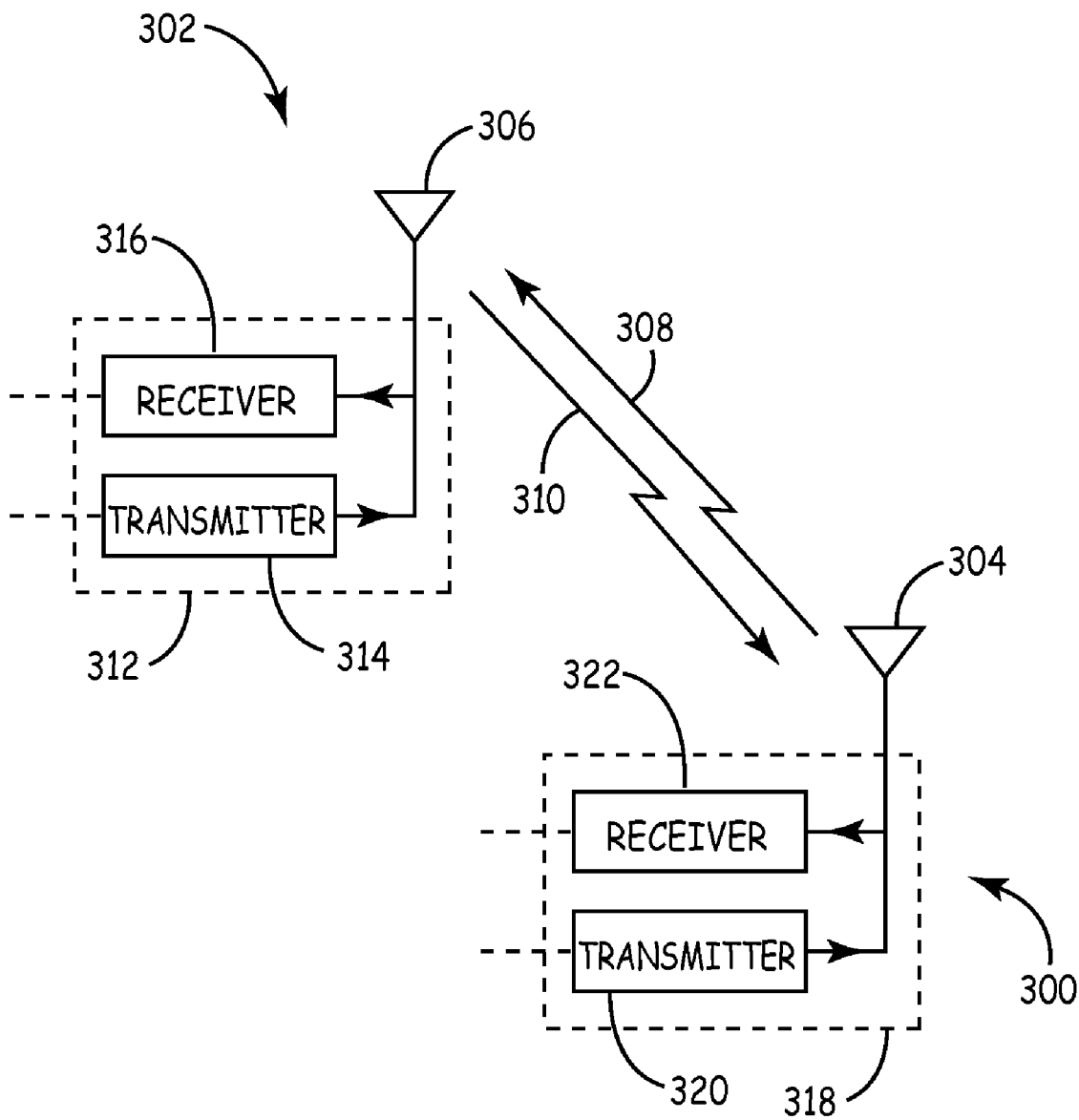
FIG. 3 is a block diagram depicting example communication modules suitable for use in an IMD communication system.

FIG. 3 depicts data communication between an IMD 300 and another device 302, which may be a device within the same body area network or any telemetry communication device. In certain embodiments, programming commands or patient data can be transmitted between one or more IMD antennas 304 associated with the IMD 300 and one or more antennas 306 associated with the device 302. In certain embodiments, a high frequency signal (or UHF, or VHF signal) can be employed. As such, it would not be necessary for antenna 306 to be held in close proximity to IMD 300. In other words, the system shown in FIG. 3 may be configured to support far field telemetry. For example, an external communication device 302 and an external communication device antenna 306 may be on a stand a few meters or so away from the patient. Moreover, the patient may be active and could be exercising on a treadmill or the like during a telemetry interrogation and transmission of real time ECG or physiologic parameters. An external communication device 302 may also be designed to universally program existing IMDs that employ the conventional ferrite core, wire coil, RF telemetry antenna of the prior art and therefore also have a conventional external communication device RF head and associated software for selective use with such IMDs.

In an uplink telemetry transmission 308, the antenna 306 operates as a telemetry receiver antenna, and the antenna 304 operates as a telemetry transmitter antenna. Conversely, in a downlink telemetry transmission 310, the antenna 306 operates as a telemetry transmitter antenna, and the antenna 304 operates as a telemetry receiver antenna. As shown with respect to FIG. 1, such telemetry transmissions may also be supported between two IMDs implanted within the same patient.

In certain embodiments, antenna 306 is electrically coupled to a telemetry transceiver or radio 312, which may include a telemetry transmitter 314 and a telemetry receiver 316. Similarly, in certain embodiments, antenna 304 is coupled to a telemetry transceiver or radio 318, which may include a telemetry transmitter 320 and a telemetry receiver 322. Referring to FIG. 2, telemetry transceiver 318 may be included within communications module 216 of the IMD 200. Alternatively, telemetry transceiver 318 may be coupled to communications module 216 to enable IMD operation as described herein. In certain embodiments, the telemetry transmitter and telemetry receiver of a given device can be coupled to control circuitry and registers under the control of a microcomputer and software maintained by the device.

In practice, the telemetered data can be encoded in any of a wide variety of telemetry formats. While not being limited to such, some examples of particular data encoding or modulation types and/or techniques that can be utilized with such data transmissions include noise modulation, general spread spectrum encoding, bi-phase encoding, quadrature phase shift keying, frequency shift keying ("FSK"), time division multiple access ("TDMA"), frequency division multiple access ("FDMA"), pre-emphasis/de-emphasis of baseband, vestigial, code division multiple access ("CDMA"), quadrature amplitude modulation ("QAM"), pi/8, quad-QAM, 256-QAM, 16-QAM, delta modulation, phase shift keying ("PSK"), quadrature phase shift keying ("QPSK"), quadrature amplitude shift keying ("QASK"), minimum shift keying, tamed frequency modulation ("TFM"), orthogonal frequency division multiplexing ("OFDM"), Bluetooth, any 802.11 modulation configuration, worldwide interoperability for microwave access ("WiMAX"), any 802.16 modulation configuration, 802.15.4, and Zigbee. Note that the "mode" used by the transceivers may be selected to optimize performance based on implant depth input and QoS input.

In certain embodiments, the uplink and downlink telemetry transmissions 308/310 between the IMD 300 and the device 302 follow a telemetry protocol that formulates, transmits, and demodulates data packets each comprising a bit stream of modulated data bits. In certain embodiments, the data packets are formulated of a data bit stream with a preamble, data and error checking data bits.

Figure 4:
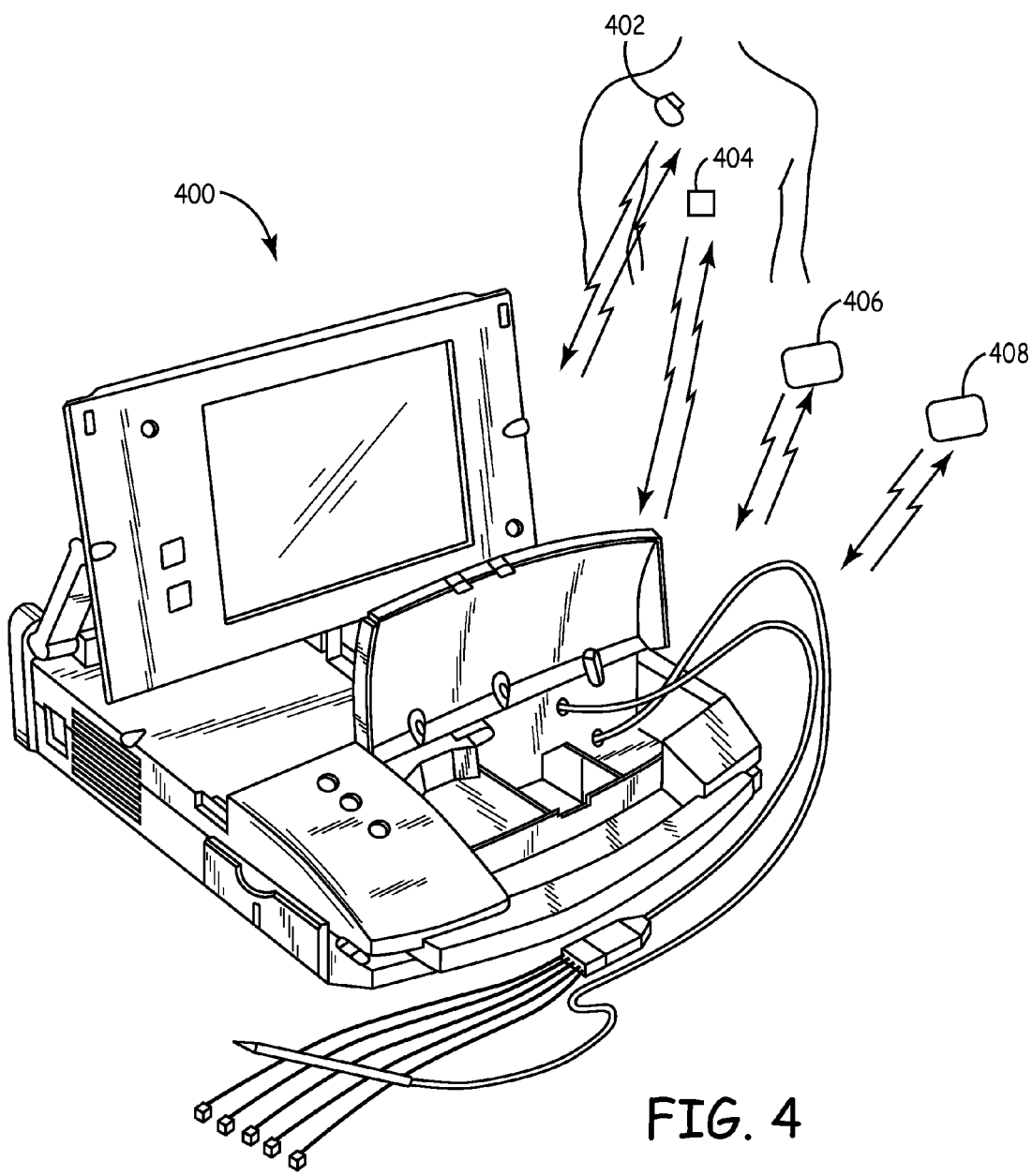
FIG. 4 is a perspective view of an external telemetry communication device configured to communicate with an IMD in accordance with certain embodiments of the invention.

In FIG. 4, there is shown a perspective view of an external device 400 configured in accordance with certain embodiments of the invention. In certain embodiments, the external device 400 can be used for telemetry communication with any number of IMDs 402/404 and/or any number of external communication devices 406/408. From such telemetry communications, the external device 400 can be subsequently used to display or further transmit patient data. The external device 400 generally includes a processing unit (not visibly shown). As should be appreciated, the processing unit can include any of a wide variety of devices. While not being limited to such, the processing unit, in certain embodiments, can be a personal computer type motherboard, e.g., a computer motherboard including a microprocessor and related circuitry such as digital memory. The details of design and operation of the computer system will not be set forth in detail in the present disclosure, as it is believed that such details are well-known to those of ordinary skill in the art. However, such external processing monitors are described in more detail in U.S. Pat. Nos. 5,345,362 and 5,683,432, which are incorporated herein by reference in their relevant parts. While not shown, it is to be appreciated that such telemetry communications between the external device 400 and the devices within the body area network (e.g., IMDs 402/404 and external communication devices 406/408) can occur in combination with telemetry communications occurring between IMDs 402/404, between external communication devices 406/408, and/or between one or more of the IMDs 402/404 and one or more of the external communication devices 406/408 (as exemplified in FIG. 1).

As described in more detail below, external device 400 may be suitably configured to function as an IMD programming device that provides data, programming instructions, and other information to an example IMD that supports power scaling. In this context, external device 400 may be a telemetry communication device that provides an implant depth value to the IMD. Moreover, a telemetry communication channel may be maintained between an IMD and external device 400 to provide quality of service information to the IMD for use during power scaling.

Figure 5:
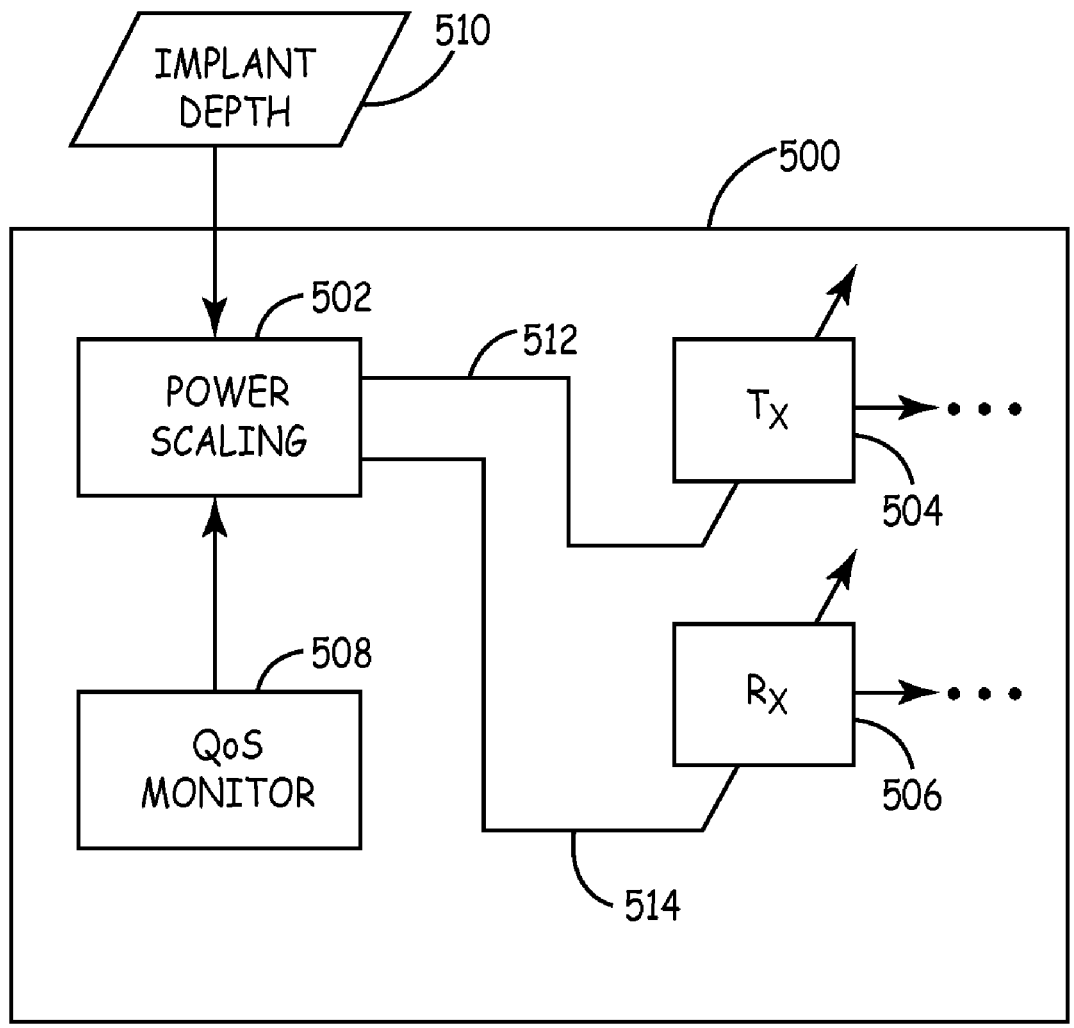
FIG. 5 a schematic representation of a portion of an example IMD that supports power scaling based upon implant depth.

FIG. 5 is a schematic representation of a portion of an example IMD 500 that supports power scaling based upon implant depth. IMD 500 is one example of an IMD that supports the implant-depth-based power adjustment techniques described herein. It should be appreciated that FIG. 5 is a very simplified depiction of a portion of IMD 500, and that an embodiment of IMD 500 will include additional components and logic that support conventional operating aspects of IMD 500. For example, an embodiment of IMD 500 may include the components and logic described above with respect to FIG. 2. IMD 500 may include power scaling logic 502, at least one transmitter 504, at least one receiver 506, and a quality of service ("QoS") monitor 508. These components and logic may be coupled as needed using any suitable interconnection architecture. In practice, transmitter 504 and receiver 506 may be realized in one transceiver or radio module.

Power scaling logic 502 is suitably configured to process an IMD implant depth value 510 in the manner described below. IMD implant depth value 510 is a piece of data that is indicative of an implant depth measurement for IMD 500. This implant depth measurement may be an actual depth measurement, a proposed or desired implant depth that is determined prior to actual implantation, a typical implant depth that represents an average acceptable depth, or the like. IMD implant depth value 510 may represent a measurement in one or more units, such as centimeters, inches, millimeters, or the like. Typical IMD implant depth measurements can range between 1.0 and 7.0 centimeters, although the invention is not limited or restricted to any particular range.

Power scaling logic 502 may receive IMD implant depth value 510 in any appropriate manner. For example, power scaling logic 502 may receive IMD implant depth value 510 from an external source such as an IMD programming device (see FIG. 4), any telemetry communication device, via manipulation of a user interface of IMD 500, via a wireless and/or wired connection to a computing device (e.g., a personal computer, a laptop computer, a personal digital assistant, etc.), from a portable data storage device, or the like. FIG. 5 depicts one possible environment where IMD implant depth value 510 is received from an external source. Although not specifically shown in FIG. 5, receiver 506 may receive IMD implant depth value 510 in a telemetry communication from an IMD programming device such that IMD 500 can process IMD implant depth value 510 in an appropriate manner and provide IMD implant depth value 510 to power scaling logic 502.

In one embodiment, IMD 500 is able to receive IMD implant depth value 510 at any designated or desired time. For example, IMD implant depth value 510 may be received from an IMD programming device prior to implantation of IMD 500, during implantation of IMD 500, and/or after implantation of IMD 500. Moreover, different IMD implant depth values 510 may be received and processed by IMD 500 to suit the actual patient needs, to suit the actual implant environment, and/or as otherwise needed to ensure proper telemetry operation of IMD 500.

Power scaling logic 502 is suitably configured to generate scaling instructions or scaling control signals in response to IMD implant depth value 510. Referring to FIG. 2, in example embodiments, power scaling logic 502 (or portions thereof) can be realized in processing unit 212, memory unit 210, and/or communication module 216. Power scaling logic 502 may include, access, or perform a power scaling algorithm, which may be realized as computer-executable program instructions. In this example, power scaling logic 502 obtains IMD implant depth value 510 and generates appropriate scaling instructions for transmitter 504 and/or for receiver 506, where such scaling instructions modify, adjust, or influence the operation of transmitter 504 and/or receiver 506. More specifically, the scaling instructions adjust variable power characteristics of transmitter 504 and/or variable power characteristics of receiver 506 in a manner that can increase battery life of IMD 500 by reducing the overall power consumption of IMD 500.

Transmitter 504 is coupled to power scaling logic 502. Transmitter 504 is configured to transmit telemetry signals from IMD 500, where such telemetry signals may be intended for any suitable device, system, or architecture (e.g., another IMD, an external programming device, a computing device, a telemetry communication device, a monitor, etc.). Transmitter 504 and IMD 500 may leverage known technologies to support telemetry communication according to accepted data transmission protocols, regulations, standards, or the like. In this embodiment, transmitter 504 is suitably configured with variable power characteristics, and is suitably configured to respond to the scaling instructions such that the scaling instructions adjust the variable power characteristics of transmitter 504. In this regard, FIG. 5 depicts a transmitter scaling control signal 512 with an arrowhead that represents adjustment of transmitter 504. The variable power characteristics of transmitter 504 may include, without limitation: the output power of transmitter 504; the gain of one or more amplifier stages in transmitter 504; a supply voltage utilized by transmitter 504; or bias current used in the transmitting stages.

A typical IMD outputs approximately 1.0 mW of power during a transmit cycle. In order to obtain this output power, the IMD may need to draw about 4.0 mA of current using a voltage supply of about 2.4 volts. In other words, the IMD will consume about 10 mW of power to generate the 1.0 mW of output transmit power. Conventional IMDs (for cardiac rhythm management devices) are usually designed to work well at a maximum implant depth of about six to seven centimeters, while other IMDs may be implanted even deeper. At a 400 MHz carrier frequency there is about 2.5 dB of attenuation per centimeter of tissue depth. By default, conventional IMDs are designed with a relatively deep implant in mind to ensure proper operation at deeper depths. In practice, however, most IMDs are implanted at shallow depths (in the range of two centimeters), which results in the IMD transmitting at an excessive power for most applications. IMD 500, however, utilizes power scaling logic 502 to adjust output power of transmitter 504 based upon the IMD implant depth value 510. This adjustment translates to a sufficiently high signal strength outside the body while conserving IMD battery life by not overdriving transmitter 504.

Receiver 506 is also coupled to power scaling logic 502. Receiver 506 is configured to receive telemetry signals intended for IMD 500, where such telemetry signals may originate at any suitable device, system, or architecture (e.g., another IMD, an external programming device, a computing device, a telemetry communication device, a monitor, etc.). Receiver 506 and IMD 500 may leverage known technologies to support telemetry communication according to accepted data transmission protocols, regulations, standards, or the like. In this embodiment, receiver 506 is suitably configured with variable power characteristics, and is suitably configured to respond to the scaling instructions such that the scaling instructions adjust the variable power characteristics of receiver 506. In this regard, FIG. 5 depicts a receiver scaling control signal 514 with an arrowhead that represents adjustment of receiver 506. The variable power characteristics of receiver 506 may include, without limitation: the gain of one or more front end components in receiver 506 (such as a low noise amplifier or a mixer); a supply voltage utilized by receiver 506; or the bias current for the receiver. Either or all of the receiver low noise amplifier, mixer, intermediate frequency amplifiers, and channel filters, may have their gains, voltage, current bias, and/or dynamic range adjusted per the implant and QoS parameters. In example embodiments, adjustment of receiver 506 may also be influenced by dynamic range requirements of receiver 506.

A typical IMD receiver is designed with a relatively high dynamic range that accommodates the projected implant depth range (about two to six centimeters in this example). Such a receiver may also employ fixed front end gain that draws about the same amount of current regardless of actual implant depth. IMD 500, however, utilizes power scaling logic 502 to adjust output power characteristics of receiver 506 based upon the IMD implant depth value 510. This adjustment may be desirable to accommodate shallow implant depth applications that require higher dynamic range for handling strong signals, less receiver sensitivity, and less front end gain. Consequently, a reduction in front end gain can translate to lower current draw and, therefore, less power consumed by IMD 500.

IMD 500 may also include QoS monitor 508, which is coupled to power scaling logic 502 in this example. QoS monitor 508 is suitably configured to process at least one QoS parameter for a communication channel between IMD 500 and a telemetry communication device (not shown in FIG. 5). In practice, if QoS monitor 508 determines that the QoS parameter satisfies minimum requirements, then power scaling logic 502 can finalize the power characteristics of IMD 500. In other words, power scaling logic 502 can fix the current adjustments corresponding to transmitter 504 and/or receiver 506. On the other hand, if QoS monitor 508 determines that the QoS parameter is insufficient or inadequate, then power scaling logic 502 may be prompted to perform additional power scaling for transmitter 504 and/or receiver 506. Note that this could be a bias to warp the gross setting of implant depth input. Due to variations in radio propagation, the QoS is highly variable and should be looked at frequently in a closed loop manner, in contrast to the implant depth, which is a fixed input.

QoS monitor 508 may generate or determine the QoS parameter(s), or it may only analyze QoS parameter(s) that IMD 500 receives from another device. In this regard, a QoS parameter may be, include, or indicate, without limitation: a link margin value; a signal-to-noise ratio; a received signal strength indicator; a bit error rate or other error indicator; or a measurement of spatial diversity antenna switching for IMD 500 (more switching indicates a weaker telemetry signal).

In alternate embodiments, some or all of the power scaling processing intelligence may reside at an IMD programming device or any telemetry communication device that can link to IMD 500. For example, an IMD programming device may include the power scaling logic and the QoS monitor elements described above. In such an embodiment, the IMD programming device may receive the IMD implant depth value, perform the power scaling routine, and generate the scaling instructions as generally described above for IMD 500. The IMD programming device, however, could then transfer the scaling instructions (and possibly the IMD implant depth value) to the IMD. Thereafter, the IMD can simply execute the scaling instructions, forward the scaling instructions to its transmitter and/or receiver, generate usable scaling control signals from the received scaling instructions, or the like.

Figure 6:
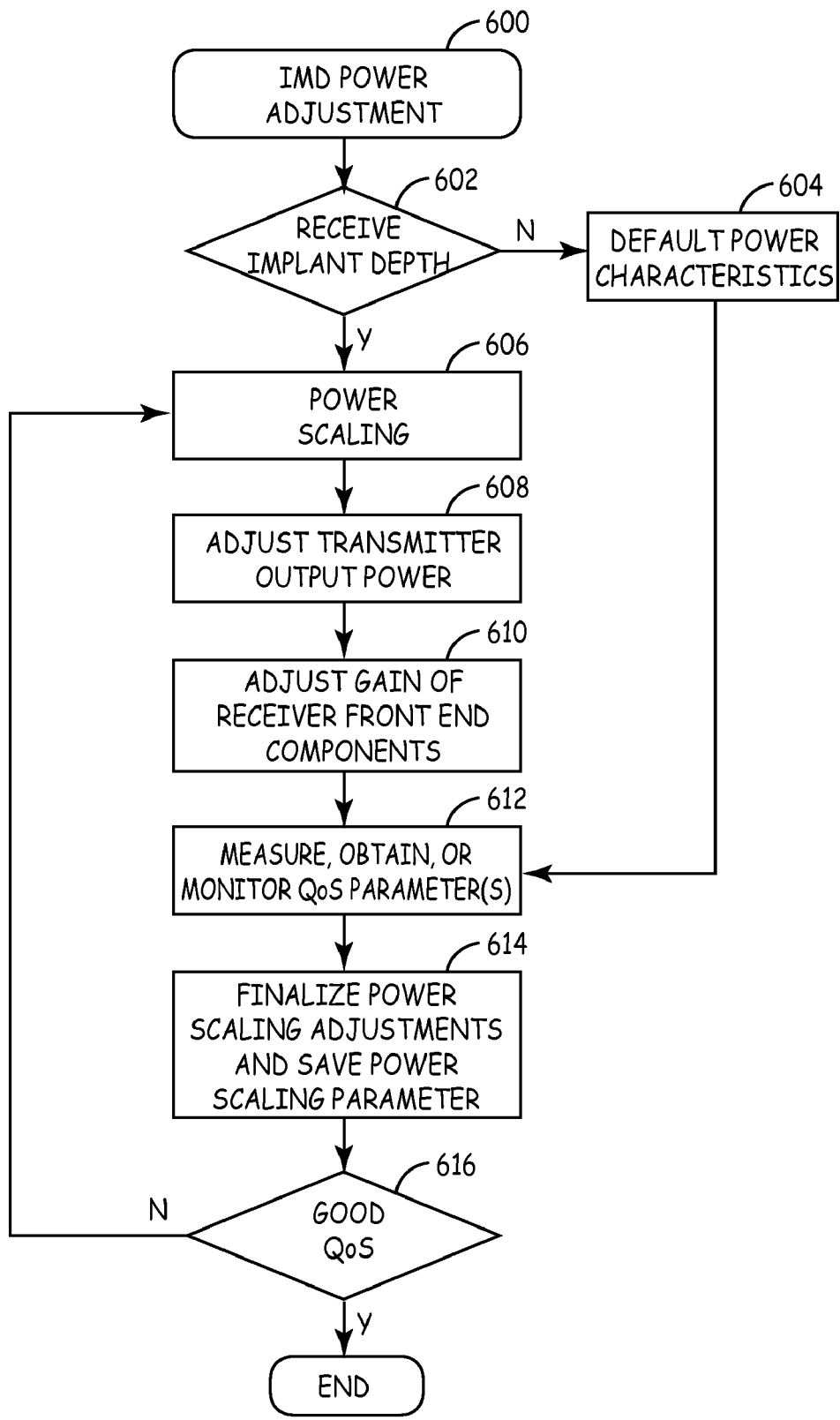
FIG. 6 is a flow chart of an IMD power adjustment process according to an example embodiment of the invention.

FIG. 6 is a flow chart of an IMD power adjustment process 600 according to an example embodiment of the invention. The various tasks performed in connection with process 600 may be performed by software, hardware, firmware, or any combination thereof. For illustrative purposes, the following description of process 600 may refer to elements mentioned above in connection with FIGS. 1-5. In embodiments of the invention, portions of process 600 may be performed by different elements of the described system, e.g., power scaling logic 502, receiver 506, or QoS monitor 508. Although process 600 considers an embodiment where the tasks are performed by an IMD, an equivalent process can be executed where at least some of the tasks are performed by an IMD programming device. It should be appreciated that process 600 may include any number of additional or alternative tasks, the tasks shown in FIG. 6 need not be performed in the illustrated order, and process 600 may be incorporated into a more comprehensive procedure or process having additional functionality not described in detail herein.

IMD power adjustment process 600 may begin by receiving an IMD implant depth value that is indicative of an implant depth measurement for the IMD (query task 602). As mentioned previously, the IMD may receive the IMD implant depth value from an IMD programming device operated by a caregiver, a surgeon, a physician, etc. Task 602 may, for example, be performed prior to implantation during a setup procedure. If process 600 does not receive an IMD implant depth value, then it may cause the IMD to utilize default power characteristics (task 604). In practice, the default power characteristics may correspond to a relatively deep implant depth that approximates the maximum allowable implant depth. Such a default setting is desirable to ensure that the IMD will support telemetry communications at any practical implant depth. If such default settings are utilized, then process 600 may proceed to a task 612 (described below).

Assuming that an IMD implant depth value is received, IMD power adjustment process 600 may perform a suitable power scaling routine for the IMD (task 606). As mentioned previously, the power scaling routine is based upon the IMD implant depth value. In this example, the power scaling logic of the IMD performs this power scaling routine to generate scaling instructions or control signals in response to the IMD implant depth value. The scaling instructions may be appropriately formatted for interpretation by the IMD transmitter, the IMD receiver, and/or the IMD transceiver, depending upon the particular implementation. For example, if the IMD implant depth value indicates a two centimeter implant depth, then the transmitter output power and receiver front end gain may be scaled down by a relatively large amount. If the IMD implant depth value indicates a four centimeter implant depth, then the transmitter output power and receiver front end gain may be scaled down by a relatively small amount. On the other hand, if the IMD implant depth value indicates a six centimeter implant depth, then the transmitter output power and receiver front end gain may not be scaled down at all.

The power scaling routine influences the adjustment of one or more power characteristics of the IMD. For example, the scaling instructions may initiate, cause, or control the adjusting of transmitter output power for the IMD (task 608), the adjusting of the gain of one or more receiver front end components for the IMD (task 610), and/or the adjusting of any parameter, quantity, feature, setting, circuit, or component of the IMD that might otherwise influence the power consumption of the IMD, including, without limitation, any of the specific items listed in the description of transmitter 504 and receiver 506 (see FIG. 5). Upon completion of this iteration of the power scaling routine, the current settings for the IMD may be temporarily saved.

In this example embodiment, IMD power adjustment process 600 measures, obtains, or monitors at least one QoS parameter for a communication channel between the IMD and a telemetry communication device (task 612). Task 612 may be performed during the implant procedure, after the implant procedure, in the context of a simulated implant procedure, etc. During task 612, the IMD or the telemetry communication device processes the at least one QoS parameter to determine whether the at least one QoS parameter satisfies minimum requirements.

Process 600 may proceed to finalize the power characteristics of the IMD by fixing the current power scaling adjustments and saving the power scaling parameter or parameters (task 614). Moreover, process 600 may perform a query task 616 to check whether the at least one QoS parameter is "good" for the particular application and operating environment, as mentioned above in the context of QoS monitor 508 (see FIG. 5). If the at least one QoS parameter meets the minimum requirements, i.e., if the QoS for the measured channel is acceptable, then process 600 may end or it may be re-entered at an appropriate place to facilitate updating as needed. On the other hand, if the QoS for the measured channel does not meet the minimum requirements, then process 600 may be re-entered at task 606. Thus, if the current power characteristics settings do not result in an acceptable QoS, then process 600 can repeat the power scaling routine to generate new power scaling instructions for the IMD. This subsequent iteration of the power scaling routine may process the at least one QoS parameter and/or data that is indicative of the level of satisfaction determined during query task 616. This additional information may be desirable to enable the power scaling routine to intelligently generate new scaling instructions to further adjust the IMD transmitter, the IMD receiver, and/or the IMD transceiver in an appropriate manner.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention, where the scope of the invention is defined by the claims, which includes known equivalents and foreseeable equivalents at the time of filing this patent application.

The invention claimed is:

1. A method for operating an implantable medical device ("IMD"), the method comprising:
   receiving an IMD implant depth value that is indicative of an implant depth measurement for the IMD;
   performing a power scaling routine for the IMD based upon the IMD implant depth value; and
   adjusting power characteristics of the IMD in response to the power scaling routine.

2. A method according to claim 1, wherein the IMD implant depth value is received from an IMD programming device prior to implantation of the IMD.

3. A method according to claim 1, wherein the implant depth measurement is between 1.0 and 7.0 centimeters.

4. A method according to claim 1, wherein adjusting power characteristics of the IMD comprises adjusting transmitter output power of the IMD.

5. A method according to claim 1, wherein adjusting power characteristics of the IMD comprises adjusting gain of receiver front end components of the IMD.

6. A method according to claim 1, further comprising:
   processing a quality of service parameter for a communication channel between the IMD and a telemetry communication device; and
   finalizing power characteristics of the IMD if the quality of service parameter satisfies minimum requirements.

7. A method according to claim 6, further comprising repeating the performing and adjusting steps if the quality of service parameter does not satisfy minimum requirements.

8. A method for operating an implantable medical device ("IMD"), the method comprising:
   the IMD receiving an IMD implant depth value from an IMD programming device, the IMD implant depth value being indicative of an implant depth measurement for the IMD;
   the IMD performing a power scaling routine to generate scaling instructions in response to the IMD implant depth value; and
   the IMD adjusting its power characteristics in response to the scaling instructions.

9. A method according to claim 8, wherein the IMD implant depth value is received from the IMD programming device prior to implantation of the IMD.

10. A method according to claim 8, wherein the implant depth measurement is between 1.0 and 7.0 centimeters.

11. A method according to claim 8, wherein the IMD adjusting its power characteristics comprises adjusting transmitter output power of the IMD.

12. A method according to claim 8, wherein the IMD adjusting its power characteristics comprises adjusting gain of receiver front end components of the IMD.

13. A method according to claim 8, further comprising:
the IMD processing a quality of service parameter for a communication channel between the IMD and a telemetry communication device; and
the IMD finalizing its power characteristics if the quality of service parameter satisfies minimum requirements.

14. A method according to claim 13, further comprising the IMD repeating the performing and adjusting steps if the quality of service parameter does not satisfy minimum requirements.

15. An implantable medical device ("IMD") comprising:
power scaling logic configured to process an IMD implant depth value that is indicative of an implant depth measurement for the IMD, and configured to generate scaling instructions in response to the IMD implant depth value; and
a transmitter coupled to the power scaling logic and configured to transmit telemetry signals, the transmitter having variable power characteristics; wherein the scaling instructions adjust the variable power characteristics of the transmitter.

16. An IMD according to claim 15, the variable power characteristics of the transmitter comprising output power of the transmitter.

17. An IMD according to claim 15, further comprising a receiver coupled to the power scaling logic and configured to receive telemetry signals, the receiver having variable power characteristics, wherein the scaling instructions adjust the variable power characteristics of the receiver.

18. An IMD according to claim 17, the variable power characteristics of the receiver comprising gain of receiver front end components of the IMD.

19. An IMD according to claim 15, further comprising a receiver coupled to the power scaling logic and configured to receive the IMD implant depth value from an IMD programming device.

20. An IMD according to claim 15, further comprising a quality of service monitor coupled to the power scaling logic, the quality of service monitor being configured to process a quality of service parameter for a communication channel between the IMD and a telemetry communication device, wherein the power scaling logic is configured to finalize power characteristics of the IMD if the quality of service parameter satisfies minimum requirements.

* * * * *